US00PP08638P

United States Patent [19]

Ackerman

[11] Patent Number: Plant 8,638

[45] Date of Patent: Mar. 15, 1994

[54] RASPBERRY PLANT NAMED PSI 744

[75] Inventor: Stephen M. Ackerman, Salinas, Calif.

[73] Assignee: Plant Sciences, Inc., Watsonville, Calif.

[21] Appl. No.: 921,716

[22] Filed: Jul. 30, 1992

[51] Int. Cl.[5] ..... A01H 5/00

[52] U.S. Cl. ..... Plt./46.2

[58] Field of Search ..... Plt. 46.2

[56] Reference Cited

U.S. PATENT DOCUMENTS

PP 8062 12/1992 Ackerman ..... Plt./46.2

*Primary Examiner*—James R. Feyrer
*Assistant Examiner*—E. F. McElwain
*Attorney, Agent, or Firm*—Foley & Lardner

[57] ABSTRACT

This invention relates to a new and distinct everbearing golden raspberry variety named PSI 744, which is capable of producing fruit on first year primocanes, and on floricanes and primocanes in subsequent years. The new variety is characterized by its moderately large peach colored fruit, moderately rugose foliage, an occasional downward crease at the apex of the terminal leaflet and an extremely thorny primocane texture.

5 Drawing Sheets

ORIGIN OF THE NEW CULTIVAR

This new variety of everbearing golden raspberry resulted from a breeding program jointly sponsored by the assignees of the application, Plant Sciences, Inc. and Coast Cooling, Inc., both of Watsonville, Calif. The breeding program had as its objective the development of new and distinct raspberry varieties. The new variety, hereinafter referred to as PSI 744, was discovered from a cross of parents 'Heritage'×'PSI-R86.138 A', an unnamed and unpatented seedling.

PSI 744 was discovered as a seedling within the population of seedlings from the stated cross. The seedling was grown and asexually propagated from root buds during the spring and summer of 1988, also in Watsonville, Calif.

After its selection in 1988, clones of the new variety were further asexually propagated and extensively tested over the next three years in advanced selection plots also located in Watsonville, Calif. This asexual propagation has demonstrated beyond question that the combination of traits disclosed herein which characterize the new variety are fixed and remain true to type through successive generations of asexual reproduction.

SUMMARY OF THE NEW VARIETY

This application relates to a new and distinct everbearing golden raspberry variety, botanically known as *Rubus idaeus*. The following characteristics are particularly distinguishing and outstanding in the new variety:

1. Everbearing fruiting habit, fruits on first year primocanes;
2. Relatively large sized, peach colored fruit having good flavor;
3. Extremely thorny texture; and
4. An occasional downward crease at the apex of the terminal leaflet.

BRIEF DESCRIPTION OF THE PHOTOGRAPHS AND FIGURE

The accompanying photographs show typical specimens of the new variety at various stages of development:

Photograph 1 shows typical plant parts of the new variety, including leaves (both upper and lower surfaces of a mature terminal leaflet), individual flowers, inflorescences, mature fruit, primocane, receptacle and the development stages of the fruit from flower to maturity;

Photograph 2 depicts a typical fruiting terminal, showing the exposure of the fruit and a notable fruit coloration;

Photograph 3 shows a typical mature terminal leaflet, with its moderate rugose texture and downward crease at the apex; and Photograph 4 shows typical plant growth and fruiting characteristics of the new variety in early September.

The FIG. 1 depicts isozyme banding patterns for PSI 744 and two closely related varieties.

Each of the four photographs were taken in Watsonville, Calif., in September 1991. Photograph 1 was taken in greenhouse filtered sunlight, while the other three photographs were taken in unfiltered outdoor light under overcast conditions.

DESCRIPTION OF THE NEW VARIETY

The following is a detailed description of the new variety, including fruit production, together with the variety's morphological, electrophoretic and pest reaction characteristics. The characteristics of the variety are compared to those of "PSI.R86.745" (U.S. Plant Pat. No. 8,062 now U.S. Plant Pat. No. 8,862, hereinafter referred to as PSI 745. This is the closest variety known to the breeder.

The detailed description of the new variety that follows is based on observations taken in August, 1991, from plants planted in Watsonville as dormant root stock in early January of the same year.

The described characteristics of the new variety may vary slightly in detail, depending upon the evaluation date and variations in environmental factors, including weather (temperature, humidity, and light intensity), day length, soil and location. PSI 744 has not been observed under all possible environmental conditions. Color terminology follows the Munsell Book of Colors, Munsell Color, Baltimore, Md. (1976).

Fruit Production

PSI 744 is primarily adapted to the climate and growing conditions of the central California coast, where it was selected and tested. This region, near the Pacific ocean, provides the necessary year-round temperatures required to produce a strong vigorous plant and remain in fruit production from August through November and later from June through July.

Initial yield studies show that PSI 744 is capable of producing moderate yields comparable to those of PSI 745 during the fall and spring months. The seasonal average fruit size, however, is less than that of PSI 745.

The new variety begins to fruit from first year primocanes in late July to early August, about the same time as PSI 745, (in some situations, a few days earlier). Peaking occurs in mid to late September, and fruiting occurs again on the floricanes in mid-June, one or two weeks later than PSI 745, peaking in early to mid-July during the spring.

Table 1 compares the fruiting characteristics of PSI 744 to those of PSI 745, the closest known variety.

TABLE 1

Comparison of late August, 1991 fresh fruit characteristics of PSI 744 and PSI 745, from fruit produced in Watsonville, California.

| CHARACTERISTICS | PSI 744 | PSI 745 |
|---|---|---|
| Munsell Surface Color | Near 5 YR 6/10 | Near 2.5 Y 8/8 |
| 1° Fruit Size L × W (cm) | 2.5 × 2.3 | 2.6 × 2.6 |
| 1° Fruit Ratio L/W | 1.09 | 1.0 |
| Seed Weight (mg) | 1.39 | 1.84 |

The fruit of PSI 744 in peach colored at maturity and typically conical in shape. Primary fruit is medium to large in size, averaging about 5.0 to 5.5 grams in weight, considerably smaller than PSI 745. The fruit size is slightly larger during the fall season, as compared to spring. The fruit is less rounded than PSI 745, as shown by the length/width ratio. The fruit cavity is medium in size and funnel shaped. Druplets are medium in size, averaging near 100 to 120 per primary berry, and typically fewer per secondary and tertiary berries. The receptacle is typically large and cone shaped, tapering to a sharp apex. Seeds are medium in size, considerably smaller than PSI 745. The variety averages 5 to 6 sepals per flower, occasionally 7. Fruit is moderately firm, separating easily from the large receptacle and possessing very good flavor. It is slightly susceptible to Botrytis fruit rot. The fruit is slightly more firm and durable in cold storage and shipping than is PSI 745.

Plant Characteristics

Selected primocane characteristics of PSI 744 are compared in Table 2 to those of PSI 745.

TABLE 2

Comparison of late August 1991 primocane characteristics of PSI 744 and PSI 745, both grown under the same conditions in Watsonville, California.

| CHARACTERISTICS | PSI 744 | PSI 745 |
|---|---|---|
| Munsell | | |
| Primocane Color | Near 5 GY 7/6 | Near 2.5 GY 6/4 |
| Floricane Color | Near 7.5 YR 5/6 | Near 5 YR 4/6 |
| Primocane Base Diameter (cm) | 1.5 | 1.3 |
| Thorn Length (mm) | 2.0 | 0.4 |
| No. Canes/Crown | 3.0 | 2.5 |
| No. Branches/Cane* | 1.7 | 0.2 |

*No. branches/cane is determined from the lower 12 inches of the primocane.

PSI 744 is a moderately dense, vigorous plant, averaging 1.5 to 1.8 meters in height, shorter than PSI 745. The plant crown produces slightly more canes than PSI 745. The plant is more upright and has a slightly darker and more dense plant canopy than does PSI 745.

PSI 744 produces many upright laterals that are moderate in strength, and support the fruit load fairly well. The primocane is medium yellow-green, with a color near 5GY 7/6, having many long and very stout thorns. This gives the primocane and extremely thorny texture, as compared to the nearly smooth textured PSI 745. Thorns are nearly the same color as the primocane, with a reddish tip and a color near 5 R 3/6. PSI 744 produces many suckers under both grower and nursery conditions. Second year floricanes are medium-brown, with a color near 7.5 YR 4/6, producing many laterals with good production late during June and July.

Foliage

PSI 744 foliage characteristics are compared to PSI 745, in Table 3. All characteristics and measurements are taken from a five-foliate.

TABLE 3

Comparison of mid-August foliage characteristics of PSI 744 and PSI 745, grown under the same conditions in Watsonville, California

| CHARACTERISTICS | PSI 744 | PSI 745 |
|---|---|---|
| Munsell Leaf Color (upper surface) | Near 7.5 GY 3/4 | Near 5 GY 3/4 |
| Petiole Length (cm) | 6.9 | 7.6 |
| Petiole Diameter (mm) | 3.5 | 3.5 |
| Terminal Leaflet Size L × W (cm) | 13.3 × 8.5 | 13.4 × 8.5 |
| Terminal Leaflet Ratio (L/W) | 1.56 | 1.58 |

The mature leaves are medium yellow-green in color, slightly darker than PSI 745. Petioles are slightly shorter in length, yet similar in diameter to PSI 745. Petiole texture is thorny with many moderately long and very stout prickles, unlike the very smooth texture of PSI 745. Mature terminal leaflets are close to the same size as PSI 745, as shown by the length×width measurement, and similar in shape to PSI 745, as shown by the length/width ratio.

Foliage is nearly always five-foliate, but occasionally a three-foliate occurs, that may develop points to true independent leaflets on the terminal leaflet. The terminal leaflet is cordate to subcordate in shape, tapering to an acuminate apex with an occasional noticeable downward crease at the apex. Surface is moderately rugose, slightly more than that of PSI 745. Foliage is primarily flat, with no notable twisting or cupping except for the occasionally creased apex.

Other Characteristics

Inflorescences are borne in cymose clusters. The fruit is well exposed, except it can be slightly concealed beneath the high number of five-foliate leaves. Flowers are medium in size, and produce ample pollen for good pollination. Flowers consist of an average of 5 to 6 obovate petals per flowers, and occasionally 7.

The new variety may not be resistant to any of the known insects and diseases common in California. It is known to be moderately susceptible to the two-spotted spider mite, powdery mildew, and yellow rust, and only slightly susceptible to Botrytis fruit rot. It has not been tested for susceptibility to Phytophthora root rot or to any of the virus complexes.

Isozymes in leaf extract

Studies of protein polymorphism in Rubus by the starch gel electrophoresis method were carried out to characterize this newly developed variety and distinguish it from similar varieties.

Isozymes were extracted from young leaves and characterized using starch gel electrophoresis techniques. The following isozymes were characterized: phosphoglucoisomerases (PGI: EC 5. 3. 1. 9) and phosphoglucomutase (PGM: EC 2. 7. 5. 1).

The plant material used was both field and greenhouse grown in Watsonville, Calif. Newly matured leaves (0.5 g fresh weight) from the growing tips of canes were used. Samples were held at 4°–8° C. and analyzed within 24 hours of collection.

The tris extraction buffer (pH 8.0) was formulated as follows: a 0.05M tris base, 0.007M citric acid (monohydrate), 0.1% cysteine hydrochloride, 0.1% ascorbic acid (Na salt or free acid), 1.0% polyethylene glycol and 80 μl/ 1 2-mercaptoethanol. Samples were extracted in a 10–12 ml cold buffer by homogenizing at 17,000 rpm or by hand grinding.

Gel and electrode buffers for the enzyme systems analyzed are given in Table 4. Electrophoresis specifications for these enzyme systems are given in Table 5.

The starch gel was prepared and held overnight at 20° C.±5° C. prior to use. The gel was prepared by dissolving potato starch (30 g) in 16 ml of cold gel buffer (System A: gel buffer 50 ml/electrode buffer 30 ml). Boiling gel buffer (220 ml) was added to the starch solution. The starch was completely dissolved and vacuumed for 15 to 30 seconds. The gel solution was immediately poured onto a 20.5 cm×22.0 plexiglass gel plate.

Samples were inoculated onto paper wicks, placed in a cooled gel (4° C.) and electrophoresed for 20 minutes. The wicks were removed, and the system run until the dye front traveled approximately 5–8 cm.

Following electrophoresis, the gel was sliced and stained for each enzyme system. Banding patterns were interpreted as they developed and gel slices were fixed in 50% glycerol.

TABLE 4

| SYSTEM | pH | GEL BUFFER | G/L | ELECTRODE BUFFER | G/L | pH |
|---|---|---|---|---|---|---|
| A | 8.3 | Tris Base | 6.5 | Lithium Hydroxide | 1.2 | 8.3 |
| | | Citric Acid (Monoh) | 1.5 | Boric Acid | 12.0 | |
| B | 7.0 | DL-Histidine HCL (Monohydrate) | 1.2 | Tris Base | 16.5 | 7.0 |
| | | | | Citric Acid (Monoh.) | 9.0 | |

TABLE 5

RUBUS ELECTROPHORESIS SPECIFICATIONS

| SYSTEM | ENZYME | pH | CURRENT | GEL SLICE |
|---|---|---|---|---|
| A | PGI | 8.3 | 275 V | 2 |
| B | PGM | 7.0 | 150 V | 3 |

The isozyme banding patterns of PSI 744 for the two enzymes systems, compared to those of Fall Gold, are shown in FIG. 1. Repetitive band intensities are given from faint to dark.

The patterns and band densities for PGI and PGM are distinctly different for PSI 744, PSI 745 and "Fall Gold". The combination of isozyme patterns shown, derived from the specific techniques described, support PSI 744 as a unique raspberry variety.

I claim:

1. A new and distinct golden raspberry variety known as PSI 744, herein described, illustrated and identified by the characteristics enumerated above.

* * * * *

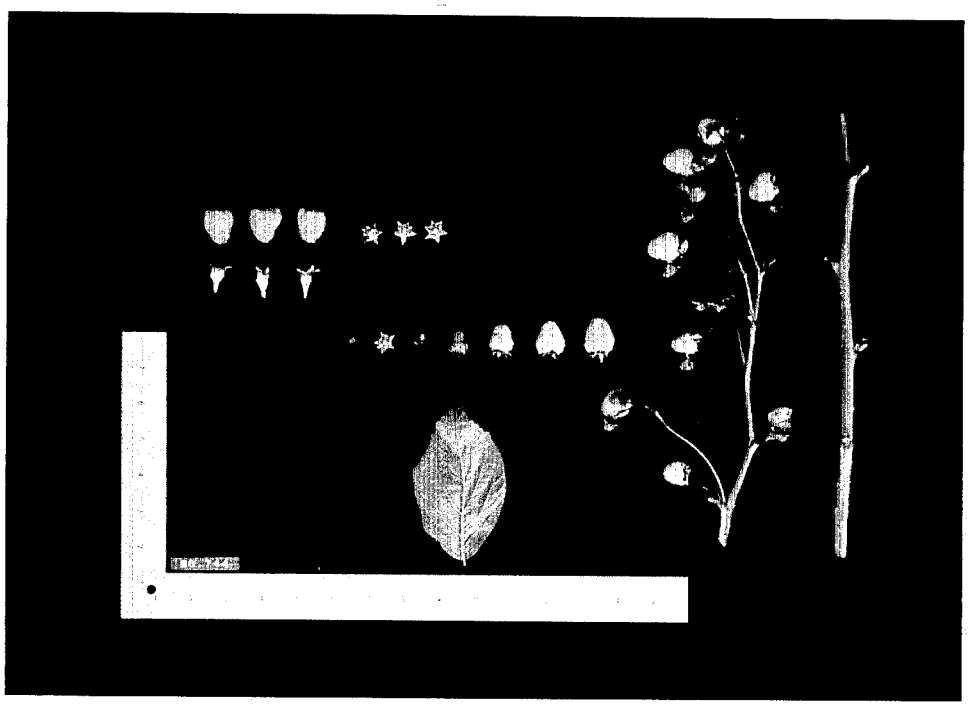

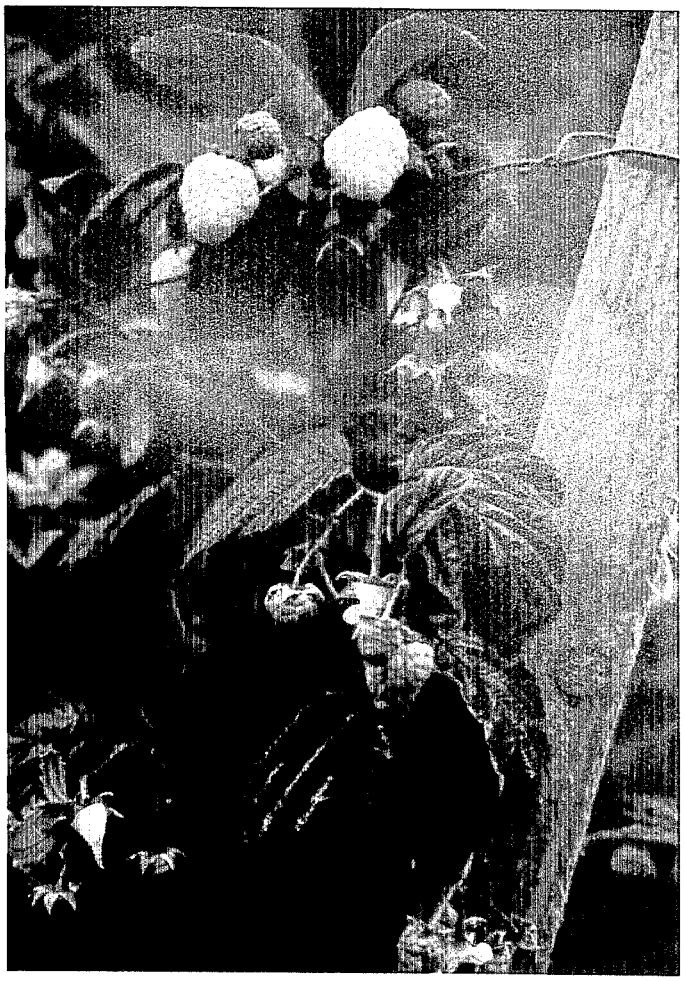

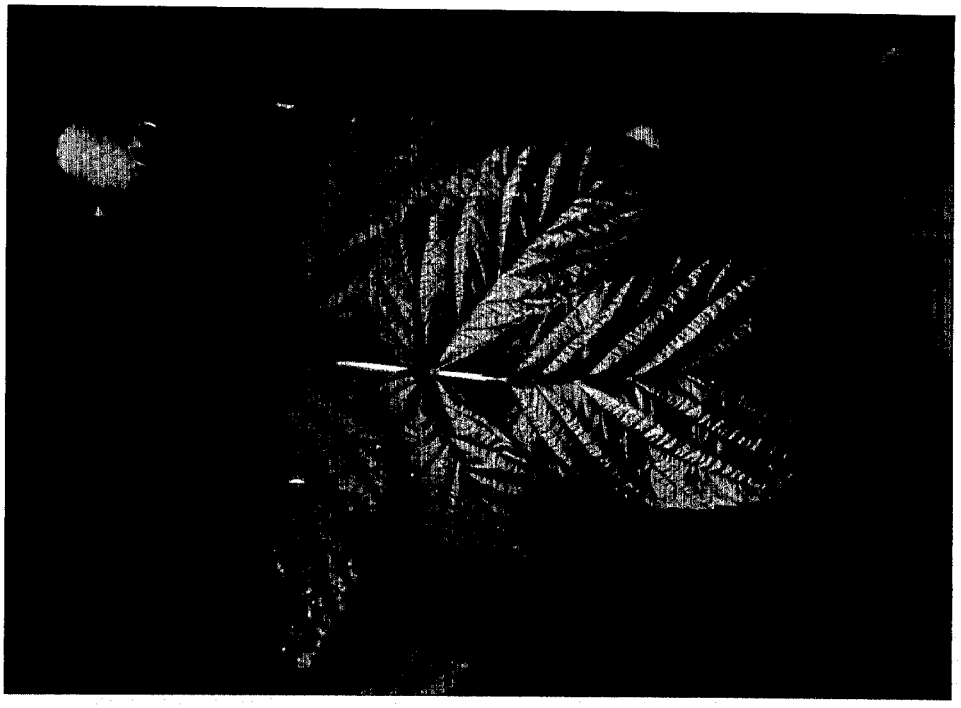

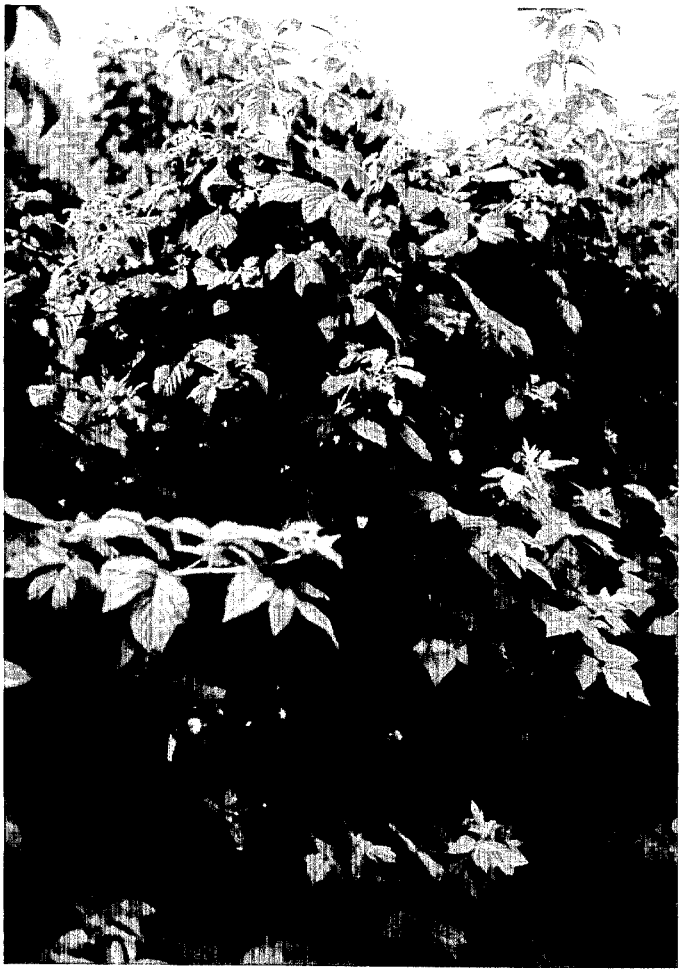

THE FIGURE
ISOZYME PATTERNS FOR '744, '745 AND FALL GOLD
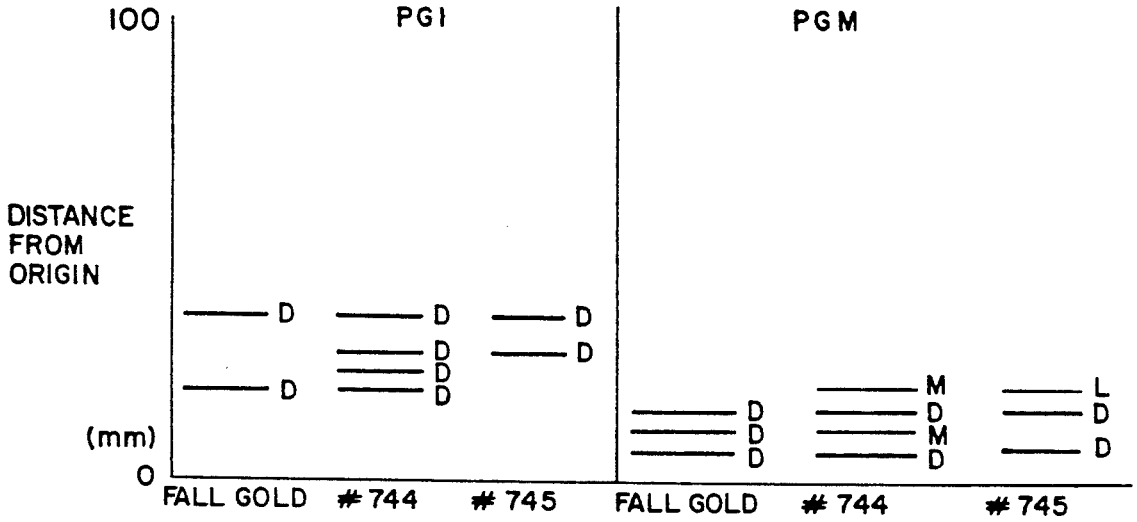
BAND INTENSITY
D = DARK
M = MODERATE
L = LIGHT